United States Patent
Kim et al.

(10) Patent No.: US 11,655,165 B2
(45) Date of Patent: May 23, 2023

(54) TANK STERILIZER

(71) Applicant: EHYGIENE CO., LTD., Ansan-si (KR)

(72) Inventors: Chan Ju Kim, Ansan-si (KR); Chae Woo Kim, Ansan-si (KR)

(73) Assignee: EHYGIENE CO., LTD., Ansan-si (KR)

( * ) Notice: Subject to any disclaimer, the term of this patent is extended or adjusted under 35 U.S.C. 154(b) by 291 days.

(21) Appl. No.: 17/112,225

(22) Filed: Dec. 4, 2020

(65) Prior Publication Data

US 2021/0206666 A1   Jul. 8, 2021

(30) Foreign Application Priority Data

Jan. 2, 2020   (KR) ........................ 10-2020-0000215

(51) Int. Cl.
*C02F 1/467* (2023.01)
*A61L 2/24* (2006.01)
*A61L 2/03* (2006.01)
*C02F 1/46* (2023.01)
*C02F 1/00* (2023.01)

(52) U.S. Cl.
CPC .............. *C02F 1/467* (2013.01); *A61L 2/035* (2013.01); *A61L 2/24* (2013.01); *C02F 1/008* (2013.01); *C02F 1/4608* (2013.01); *A61L 2202/11* (2013.01); *A61L 2202/122* (2013.01); *A61L 2202/14* (2013.01); *C02F 2201/4614* (2013.01); *C02F 2201/4616* (2013.01); *C02F 2209/05* (2013.01); *C02F 2303/04* (2013.01)

(58) Field of Classification Search
USPC ........................................................ 210/143
See application file for complete search history.

(56) References Cited

U.S. PATENT DOCUMENTS

2010/0135869 A1* 6/2010 Shiue .................... C02F 1/4672
422/186.08

FOREIGN PATENT DOCUMENTS

| | | |
|---|---|---|
| JP | H11300359 A | 11/1999 |
| JP | 2013086031 A | 5/2013 |
| JP | 2018053318 A | 4/2018 |
| JP | 2018108555 A | 7/2018 |
| KR | 200227807 | 6/2001 |
| KR | 20050063859 | 6/2005 |
| KR | 20120133230 | 12/2012 |
| KR | 20180117236 | 10/2018 |

\* cited by examiner

*Primary Examiner* — Hayden Brewster
(74) *Attorney, Agent, or Firm* — Cantor Colburn LLP

(57) ABSTRACT

Provided is a tank sterilizer composed of a power supply part including an operation switch, and a sterilization part for sterilizing fluid in a tank, wherein a sterilization effect is maximized by generating microbubbles by electrolysis or electric discharge instead of killing bacteria by using a UV LAMP, an ozone lamp, and a pressure pump, and due to the coupling of a bubble generation module and a power connection module to each other by an electroconductive connector, a separate power connector is not required to be installed, whereby the tank sterilizer is simple in structure and is easy to be installed.

4 Claims, 5 Drawing Sheets

TANK STERILIZER

BACKGROUND OF THE INVENTION

Field of the Invention

The present disclosure relates generally to a tank sterilizer. More particularly, the present disclosure relates to a tank sterilizer, which is composed of a power supply part including an operation switch, and a sterilization part for sterilizing fluid in a tank, wherein a sterilization effect is maximized by generating microbubbles by electrolysis or electric discharge instead of killing bacteria by using a UV LAMP, an ozone lamp, and a pressure pump, and due to the coupling of a bubble generation module and a power connection module to each other by an electroconductive connector, a separate power connector is not required to be installed, whereby the tank sterilizer is simple in structure and is easy to be installed.

Description of the Related Art

Generally, fluid in a tank for drinking or washing, etc. may be easily contaminated biologically by contact with air. Therefore, it is common to install a sterilizer such as an ultraviolet sterilizer in the tank in order to eliminate this problem.

As such a prior art, "Sterilizing device for water" is proposed in Korean Utility Model Registration No. 20-0227807.

The sterilizing device for water includes: a water collection tank 10 storing water; a pumping part 40 connected from the water collection tank 10 to a circulation pipe 20; and a sterilization part 50 connected from the pumping part 40 to the circulation pipe 20, and to the water collection tank 10, wherein the sterilization part 50 includes: the sterilization tank 51 having a box shape; a UV lamp 52 installed in the sterilization tank 51 at an upper side thereof; a negative ion generation part 53 installed inside the sterilization tank 51; an ozone generation part 54 generating ozone O3 inside the sterilization tank 51; and an ultrasonic generation part 55 composed of an ultrasonic oscillator 55a sending an ultrasonic wave to the inside of the sterilization tank 51 and an ultrasonic vibration part 55b.

However, water treated by an ultraviolet-type sterilization device of the prior art does not have remaining sterilizing substances having sterilizing power, and thus water in a water storage tank is contaminated again due to additional biological contamination, that is, due to the propagation of harmful bacteria occurring in the water storage tank.

Accordingly, to solve such a problem, as a prior art, "A tank sterilization device by a current conduction method" is proposed in Korean Patent Application Publication No. 10-2005-0063859.

The prior art proposes the tank sterilization device by the current conduction method, the tank provided to store and drink pretreated water, the device including: a sterilizer 20 installed inside the tank and configured as a casing body having multiple holes 25 formed therein, wherein minerals 23 adsorbing harmful components remaining in water are filled inside the casing body, and sealed charcoal parts 26 connected to a (+) pole and a (−) pole of an electric wire 30 and filters 27 formed outside the charcoal parts 26 are provided at the center part of the casing body.

However, the tank sterilization device of the prior art uses sealed charcoal, and the charcoal is not efficiently supplied and is difficult to be semipermanently used. Accordingly, a new type of sterilization device is required.

SUMMARY OF THE INVENTION

Accordingly, the present disclosure has been made keeping in mind the above problems occurring in the related art, and the present disclosure is intended to propose a tank sterilizer which is composed of a power supply part connected to external power, and a sterilization part including a bubble generation module sterilizing fluid in a tank by generating microbubbles, whereby a sterilization effect is increased and the fluid is prevented from being contaminated again.

Particularly, the present disclosure is intended to propose a tank sterilizer, in which when the power supply part supplies electricity to the bubble generation module, mechanical and electrical connections between the power connection module and the bubble generation module are simultaneously made by a connector made of an electroconductive material.

In addition, the present disclosure is intended to propose a tank sterilizer, in which a power connection module transferring electricity to the bubble generation module is configured to be integrated with a tank as a part of the tank such the tank has a sterilization function.

In order to achieve the above objectives, according to one aspect of the present disclosure, there is provided a tank sterilizer including: a power supply part connected to external power; a power connection module being electrically conductive with the power supply part through a power supply line; and a bubble generation module mounted removably to the power connection module by a connector, wherein the connector is made of a conductive material, and electricity conducted to the power supply part is supplied to the bubble generation module by the connector such that the bubble generation module generates microbubbles and sterilizes fluid in a tank.

As described above, the tank sterilizer according to the present disclosure is composed of the power supply part and the sterilization part, and allows microbubbles to be generated in the sterilization part so as to sterilize fluid in the tank, thereby maximizing a sterilization effect and preventing the change of fluid properties occurring when using UV.

Furthermore, in the tank sterilizer, the power connection module and the bubble generation module constituting the sterilization part are configured to be mechanically and electrically coupled to each other by the connector made of an electroconductive material, thereby simplifying the structure of the tank sterilizer.

Additionally, the power connection module is configured as a part of the tank, thereby supplying a sterilization function to the tank.

In addition, currents having different magnitude are supplied according to the properties of fluid by a controller such that microbubbles are generated regardless of the fluid, thereby improving a sterilization effect.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
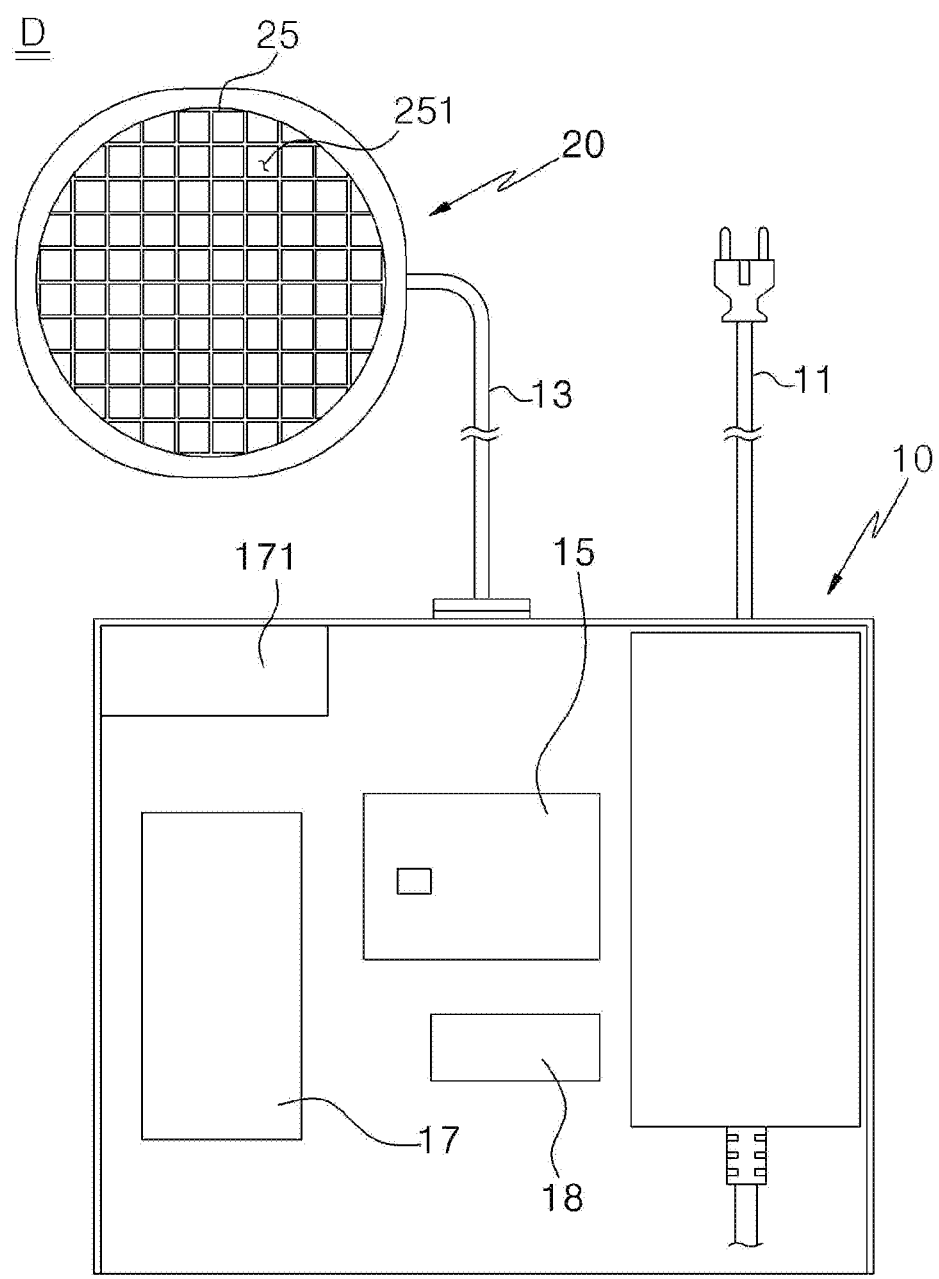
FIG. 1 is a view roughly illustrating a tank sterilizer according to the present disclosure.

Hereinbelow, a tank sterilizer of the present disclosure will be described in detail with reference to the accompanying drawings.

The tank sterilizer of the present disclosure may be variously modified and may have various shapes, and will be described in detail based on aspects (or embodiments). However, the present disclosure should not be construed as being limited to only the embodiments set forth herein, but should be construed as covering modifications, equivalents, or alternatives falling within ideas and technical scopes of the present disclosure.

In each drawing, like reference numerals, particularly, tens and units, or reference numerals having like tens, units and letters refer to like elements having like functions throughout, and unless the context clearly indicates otherwise, elements referred to by reference numerals of the drawings should be understood based on this standard.

In addition, for convenience of understanding of the elements, in the figures, sizes or thicknesses may be exaggerated to be large (or thick), may be expressed to be small (or thin), or may be simplified for clarity of illustration, but due to this, the protective scope of the present disclosure should not be interpreted narrowly.

The terminology used herein is for the purpose of describing particular aspects (or embodiments) only and is not intended to be limiting of the present disclosure. As used herein, the singular forms are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present disclosure belongs. It will be further understood that terms used herein should be interpreted as having a meaning that is consistent with their meaning in the context of this specification and the relevant art and will not be interpreted in an idealized or overly formal sense unless expressly so defined herein.

The present disclosure relates to a tank sterilizer D, and the tank sterilizer includes a tank that stores fluid used for drinking and washing. The feature of the present invention is that the fluid in the tank is sterilized by generating microbubbles without using a UV lamp or the like.

First, microbubbles have been verified as effective for sterilization and antibacterial processes in various experiments, and thus are applied to various products such as a showerhead and a washing machine.

The tank sterilizer of the present disclosure is designed to sterilize fluid in the tank by generating microbubbles having a high sterilization effect in the tank. As illustrated in FIG. 1, the tank sterilizer is composed of a power supply part 10 and a sterilization part 20, and is configured to generate the microbubbles by immersing the sterilization part 20 in the tank.

First, the power supply part 10 is provided outside the tank, and is configured as a casing body having a receiving part formed therein, wherein an external power cable 11 is provided at a side of the casing body to supply electricity by being connected to external power, and a power supply line 13 is provided by protruding from the inside of the casing body to supply the electricity to the sterilization part 20. The external power cable 11 and the power supply line 13 are electrically connected to each component provided inside, that is, to a controller 15 and a register 17 to be described later, which will be described more in detail below.

In addition, the casing body is configured to have an operation switch therein such that the operation of the sterilization part 20 is controlled by the operation switch.

The sterilization part 20 will be described more in detail with reference to FIGS. 1 and 2. The sterilization part 20 is configured by including a power connection module 21 receiving electricity by being connected to the power supply line 13 extending from the power supply part 10, and a bubble generation module 23 electroconductively coupled to the power connection module 21 and generating microbubbles.

First, the embodiments of the present disclosure may be composed of a first embodiment in which the power connection module 21 is configured as a plate-shaped member, and a second embodiment in which the power connection module 21 is configured as a part of a tank housing.

Figure 2:
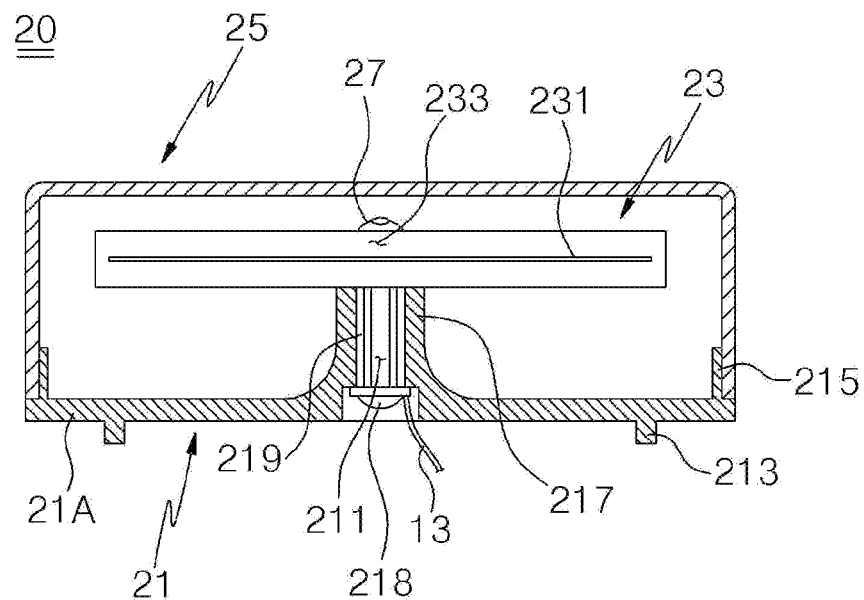
FIG. 2 is a detailed view of a sterilization part of the tank sterilizer according to the present disclosure a sterilization part.

As illustrated in FIG. 2, in the first embodiment, the power connection module 21 and a protection cover 25 to be described later are configured to form one casing, wherein the casing is arranged inside the tank such as on a lower or side surface of the tank so as to sterilize fluid in the tank.

Although not shown, in the second embodiment, the power connection module 21 is configured as a part of the tank, wherein the protection cover 25 is coupled to or attached to the power connection module 21 to perform a sterilization function in the tank.

Accordingly, in the first embodiment, the power supply line 13 connected to the power connection module 21 is immersed in fluid in the tank, and in the second embodiment, the power supply line 13 located outside the tank is connected to the tank. In the case of the first embodiment, the power supply line is preferably waterproofed with epoxy, etc.

According to the first embodiment of the present disclosure, the tank sterilizer will be described more in detail below. The power connection module 21 is configured as a base 21A having a bolting hole 211 formed in a center thereof, wherein support protrusions 213 are provided on the lower surface of the base 21A and are configured to secure space through which the power supply line 13 passes when connecting the power supply line 13, and an inner flange part 215 is formed on an edge of the base 21A by protruding inward therefrom such that the protection cover 25 is in close contact with and fitted over the outer surface of the inner flange part 215, or is coupled to the inner flange part by a fastening unit to be described later.

In addition, the bolting hole 211 is preferably formed in a protrusion 217 protruding from the center of the base 21A.

The bubble generation module 23 sits on and is coupled to the protrusion 217 so as to discharge microbubbles in all directions.

Furthermore, the protection cover 25 is coupled to the power connection module 21, and is configured to include a plurality of discharge holes 251 as illustrated in FIG. 1 such that the microbubbles generated by the bubble generation module 23 are discharged.

A bolt 218 for supplying power is fastened to the bolting hole 211 such that electricity is transferred to the power connection module 21. The power supply line 13 is connected to the bolt 218 and an insert nut 219 is preferably provided in the protrusion 217 such that the bolt 218 is fastened to the insert nut. Specifically, the insert nut 219 is conductive and provided in the protrusion 217, the bolt 218 for supplying power is fastened to the bolting hole 211 in the lower part of the insert nut 219, the power supply line 13 is connected to the bolt 218, and the bolt 218 is conductive and fastened as a connector 27 to the upper part of the insert nut 219, thereby fixing the bubble generation module 23 seated in the protrusion 217.

In addition, when receiving electricity, the bubble generation module 23 is intended to emit microbubbles to the outside by discharging, and is configured by including an electrode plate 231, wherein a connection hole 233 is provided in the bubble generation module 23, and a connector 27 is configured to be fastened to the connection hole 233 such that the connector is fastened to the power connection module 21, more precisely, to the protrusion 217.

More precisely, the connector 27 is made of a conductive material such as a bolt or pin to conduct electricity, and is fastened to the bolting hole 211 of the protrusion 217 by passing through the connection hole 233, whereby the connector is configured to allow the bubble generation module 23 to be mechanically coupled to the protrusion 217 and at the same time, to be electrically coupled to the protrusion 217 to be electrically conductive therebetween.

The generation of microbubbles by the tank sterilizer of the present disclosure will be described in detail below. Microbubbles refer to small bubbles that are produced by water and air alone without adding chemicals. In the process of the generation and extinction of such bubbles, as instantaneous ultra-high temperature (4000° C.) and ultra-high pressure conditions are induced, a hot ultrasound wave is generated and a large amount of negative ions are released. Due to this negative ion release, a sterilization function and a purification effect may be expected.

Various methods of generating such microbubbles are known, but the tank sterilizer of the present disclosure generates the microbubbles by using underwater electric discharge by the electrode plate.

More specifically, this underwater electric discharge decomposes water molecule ions into hydrogen ions and oxygen ions through a strong discharge effect. In the state in which the ions are activated, the ions are combined into substances having strong sterilizing power such as hydroxide ions, slightly acidic hypochlorous acid water, or hydrogen peroxide, and in this process, hydroxide ions are generated.

In this process, the bubbles in the form of the microbubbles become smaller and shrink into nanobubbles, generating hydroxyl radicals. Hydroxyl radicals are known to be excellent in sterilization power and in the ability of decomposing non-degradable organic materials.

In addition, since ultra-high pressure acts inside the gases of such bubbles, the amount of dissolved oxygen inside water may be expected to increase.

Figure 3:
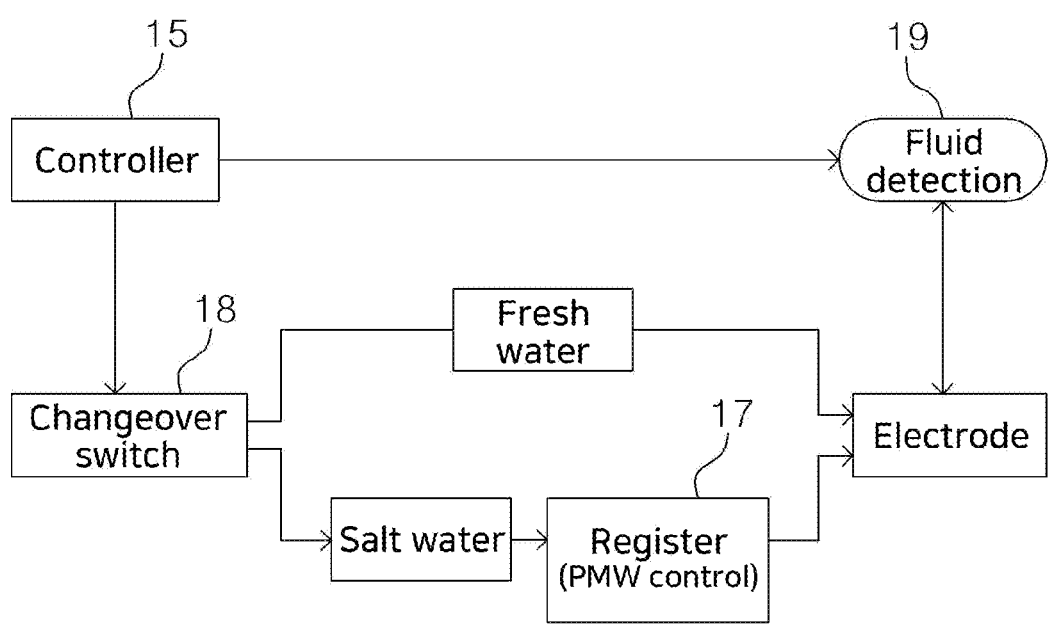
FIG. 3 is a block diagram illustrating the operation of a power supply part of the tank sterilizer according to the present disclosure a power supply part.

FIG. 3 is a block diagram illustrating the operation of the tank sterilizer according to the present disclosure. The tank sterilizer of the present disclosure is configured to control the intensity of current according to the type of fluid in the tank such that microbubbles are constantly generated regardless of the type of the fluid.

Generally, fluid may be classified into salt water and fresh water depending on the presence or absence of salt (NaCl). Salt water and fresh water have the difference of at least 100 times in electrical conductivity therebetween, and thus current is required to be supplied by controlling the intensity of the current according to the type of fluid such that the microbubbles are generated and electric and electronic parts are protected.

To this end, the controller 15, the register 17, a changeover switch 18, and a detection part 19 are provided in the power supply part 10.

More specifically, the controller 15 is intended to control the flow of current. First, the detection part 19 transfers a detection current to the bubble generation module 23, and then detects a current value which varies according to different electrical conductivity for each type of fluid, and transfers the detected current value to the controller 15.

In this case, a threshold value to distinguish salt water from fresh water is set and stored in the controller 15, and when the detected current value exceeds the threshold value, the fluid is recognized as salt water, and when the detected current value is the threshold value or less, the fluid is recognized as fresh water.

When the controller 15 recognizes the fluid as salt water, the changeover switch 18 operates to transfer the current to the register 17 such that the current is lowered to the set threshold value and then the lowered current is transferred to the bubble generation module 23. When the controller 15 recognizes the fluid as fresh water, the changeover switch 18 operates to allow the current to be transferred directly to the bubble generation module 23 without flowing through the register 17 such that microbubbles are generated.

Furthermore, it is possible to lower the current by using PMW control in addition to the register 17, and the scope of the claims should not be interpreted as being limited thereto.

That is, due to such an operation according to the present disclosure, microbubbles are constantly generated in spite of the difference of electrical conductivity between fresh water and salt water, so fluid in the tank is sterilized more effectively.

In addition, to prevent the register 17 from overheating, a separate cooling fan 171 may be provided, but the scope of the claims should not be interpreted as being limited thereto.

Figure 4:
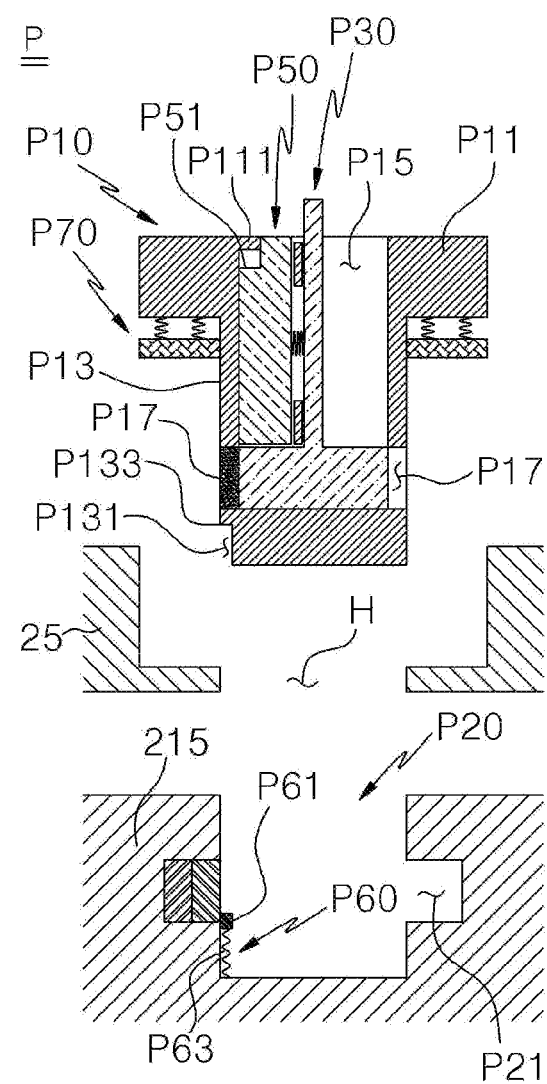
FIGS. 4 to 6 are sectional views of a fastening unit by which a protection cover and a power connection module of the tank sterilizer according to the present disclosure are coupled to each other.
Figure 5:
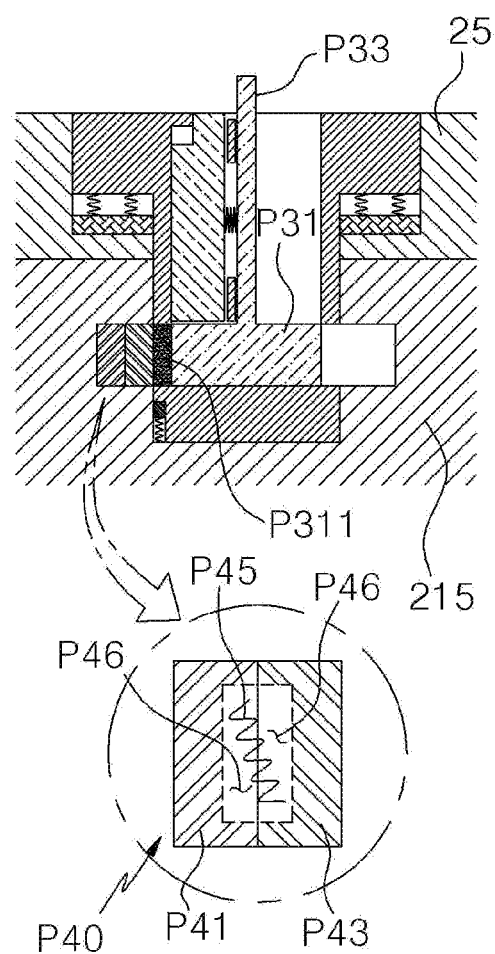
Figure 6:
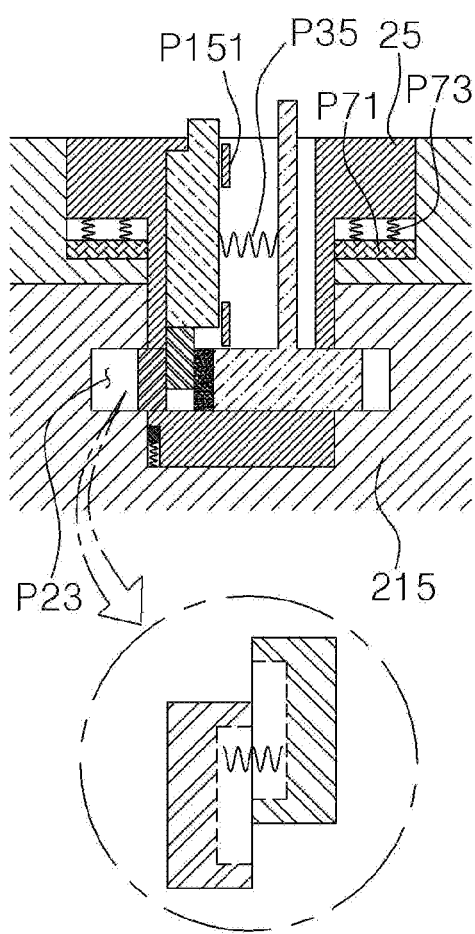

Referring to FIGS. 4 to 6, the protection cover 25 is configured to be more easily mounted to and be removed from the power connection module 21 by the fastening unit, so during the maintenance of the bubble generation module 23 inside the protection cover 25, the protection cover 25 can be easily removed from the power connection module.

The fastening unit P is configured by including: a fastening pin P10 composed of a body part P13 passing through a coupling hole H of the protection cover 25 and a head part P11 provided on the upper part of the body part P13 and pressing a surface of the protection cover 25; a pin groove P20 formed in the inner flange part 215 to fit the fastening pin P10 thereto; and a fastening member P30 provided in the fastening pin P10, the fastening member fitting the fastening pin P10 to the pin groove P20. Each part of the fastening unit will be described more in detail with reference to FIGS. 4 to 6.

In addition, for convenience of description, the fitting direction of the fastening pin P10 is set from an upper side toward a lower side relative to FIG. 4, but the scope of the claims should not be interpreted as being limited thereto.

First, the fastening unit P is configured by including: the fastening pin P10 composed of the head part P11, the body part P13, a center groove P15 formed in the center of the fastening pin, and a withdrawal hole P17 formed in the lower part of the center groove P15 toward opposite sides thereof; the pin groove P20 formed in the inner flange part 215 and to which the body part P13 is inserted, wherein a seat groove P23 and a holding groove P21 are formed at the opposite surfaces of the pin groove such that each of the seat groove and the holding groove corresponds to the withdrawal hole P17; the fastening member P30 including: a fastening body P31 provided to be inserted into the center groove P15 of the fastening pin P10 and to withdraw through the withdrawal hole P17, the fastening body having a magnet P311 formed at a second end thereof, and a handlebar P33 provided on the fastening body P31 and exposed to the upper side of the fastening pin P10 through the center groove P15; and an insertion prevention member P40 provided in the seat groove P23 and configured by including a support block P41, a metal raising/lowering block P43 coupled to the support block P41 to raise and lower therefrom, and a raising induction spring P45 giving an elastic force to the raising/lowering block P43, wherein when the fastening member P30 is advanced after being inserted to the center groove P15, the fastening body P31 is withdrawn through the withdrawal hole P17 and inserted to the holding groove P21, so the removal of the fastening pin P10 is prevented, and when the fastening body P31 is inserted to the holding groove P21, the insertion prevention member P40 is pulled to the fastening pin P10 by the magnet P311 of the fastening body P31. In this case, the raising/lowering block P43 is raised from the support block P41 by the raising induction spring P45 and supports the inner wall surface of the center groove P15, so that the backward movement of the fastening member P30 is limited.

More specifically, the fastening pin P10 is composed of the head part P11 and the body part P13 and has a pin shape. The fastening pin is preferably configured as a quadrangular pin rather than a cylindrical pin such that the fastening pin has directionality. Correspondingly, the pin groove P20 is also preferably configured as a groove having a quadrangular shape, and the center groove P15 is also preferably configured as a quadrangular shape. A display part may be formed on the fastening pin P10 to indicate direction, but the scope of the claims should not be interpreted as being limited thereto.

To describe again, the fastening pin P10 has the center groove P15 formed therein, and the center groove P15 is a groove formed in the center of the fastening pin P10. The withdrawal hole P17 is formed at each of the opposite sides of the lower surface of the center groove P15, and is configured to allow the withdrawal of the fastening body P31 and the insertion of the insertion prevention member P40 to be described later.

The fastening member P30 composed of the fastening body P31 and the handlebar P33 is provided in the center groove P15 of the fastening pin P10.

The fastening body P31 is a member formed to withdraw through the withdrawal hole P17 by being in close contact with the lower surface of the center groove P15. The handlebar P33 is provided by protruding upward from the fastening body P31, and refers to a member having the shape of a rectilinear bar protruding (being exposed) to the upper side of the center groove P15.

Accordingly, when a user grasps and moves the handlebar P33, the first end of the fastening body P31 is configured to withdraw to a side of the body part P13 of the fastening pin P10 through the withdrawal hole P17.

In addition, the magnet P311 is provided at the second side of the fastening body P31 and is intended to pull the insertion prevention member P40 described below, which will be described below.

The pin groove P20 is a place to which the body part P13 of the fastening pin P10 is inserted, and is configured to have the holding groove P21 formed at a first side of the pin groove and the seat groove P23 formed at a second side thereof so as to correspond to the withdrawal hole P17, wherein the insertion prevention member P40 is received in the seat groove P23.

The operating method of the fastening pin will be roughly described. To couple the protection cover 25 to the power connection module 21, after the fastening pin P10 passes through the coupling hole H formed in the protection cover 25 such that the head part P11 presses the protection cover 25, the fastening pin P10 is fitted in the pin groove P20. Next, when a user advances the first end of the fastening body P31 to the holding groove P21 by manipulating the handlebar P33 exposed to the upper side of the fastening pin P10, the fastening pin P10 is held in the pin groove P20. In this case, when the magnet P311 provided on the second end of the fastening body P31 pulls the insertion prevention member P40 received in the seat groove P23, the raising/lowering block P43 of the insertion prevention member P40 is raised inside the center groove P15, and supports the inner surface of the body part P13, that is, the wall surface of the center groove P15, so that the backward movement of the fastening body P31 is limited and the fastening member P30 is prevented from being randomly manipulated.

To this end, the raising/lowering block P43 is made of metal such that the raising/lowering block is pulled by the magnet P311.

To this end, the insertion prevention member P40 is received in the seat groove P23, and is composed of the support block P41 and the raising/lowering block P43 provided to slide on the support block P41, wherein the raising induction spring P45 is provided between the raising/lowering block P43 and the support block P41, and gives an elastic force to the raising/lowering block P43 to raise the raising/lowering block P43.

In this case, the raising induction spring P45 may be configured as a normal spring or a coil spring coupled to the support block P41 and the raising/lowering block P43 at opposite end parts thereof, but the scope of the claims should not be interpreted as being limited thereto.

For example, groove parts P46 communicating with each other are formed in the meeting surfaces of the raising/lowering block P43 and the support block P41 each other, wherein the raising induction spring P45 is provided in the groove parts P46 and may give an elastic force to the raising/lowering block P43 to raise the raising/lowering block.

As a result, when the insertion prevention member P40 is received in the seat groove P23, the rising of the raising/lowering block P43 is prevented by the upper surface of the seat groove P23, but when the insertion prevention member P40 is pulled through the withdrawal hole P17 by the fastening pin P10 and the raising/lowering block P43 is located inside the center groove P15, there is no component supporting the upper surface of the raising/lowering block P43, so the raising/lowering block P43 is raised by the elastic force of the raising induction spring.

To perform the release of the fastening pin P10 from the pin groove P20, a member for forcibly lowering the raised raising/lowering block P43 is required. To this end, a push member P50 is provided in the fastening pin P10, more precisely, in the center groove P15.

The push member P50 is located at the left side of the center groove P15 relative to the drawings and is a member whose lower surface sits on the fastening body P31.

That is, as illustrated in FIG. 6, when the raising/lowering block P43 is raised inside the center groove P15, the raising/lowering block pushes the push member P50 and the upper end part of the push member P50 is exposed to the outside of the center groove P15. When a user presses the exposed part, the raising/lowering block P43 is lowered and the release of the fastening pin P10 is performed.

Furthermore, a removal prevention step P111 preventing the push member P50 from being removed to the outside of the center groove P15 is provided in the head part P11, and a holding step P51 held in the removal prevention step P111 is provided in the push member P50.

To prevent the push member P50 from moving in a side-to-side direction (relative to FIG. 4) inside the center groove P15, at least one removal prevention protrusion P151 limiting the movement of the push member P50 is provided on the wall surface of the center groove P15.

Due to such a configuration, the push member P50 may move only in a vertical direction.

Furthermore, to facilitate the release of the fastening pin P10 and to prevent the withdrawal of the fastening body P31 through the withdrawal hole P17 during the storage of the fastening pin P10, an elastic spring P35 is provided.

The opposite ends of the elastic spring P35 are in close contact with the push member P50 and the handlebar P33 therebetween, and the elastic spring is configured to give an elastic force to the handlebar P33 in a left direction, that is, in a direction toward the push member P50.

Accordingly, normally, as illustrated in FIG. 4, the fastening member P30 is stably located in the center groove P15. When a user inserts the fastening body P31 to the holding groove P21 by moving the fastening member P30, the elastic spring P35 is tensioned as illustrated in FIG. 6. In this case, since the raising/lowering block P43 is raised, the fastening body P31 is not restored to an initial position thereof in spite of the elastic force of the elastic spring.

During the release of the fastening pin P10, when a user lowers the raising/lowering block P43 by pressing the push member P50, the fastening member P30 is moved backward by the elastic force of the elastic spring P35, and the first end of the fastening body P31 is released from the holding groove P21. In cooperation with this operation, the insertion prevention member is restored to the initial position thereof by being pushed into the seat groove P23, and then the fastening pin P10 can be removed from the pin groove P20.

In addition, the tank sterilizer of the present disclosure further includes a stopping member P60 for preventing the insertion prevention member received in the seat groove P23 from being removed therefrom.

The stopping member P60 is provided on the lower surface of the pin groove P20, and includes a stopper P61 and a stopping spring P63 giving an elastic force to the stopper P61. Although not shown, the stopper P61 is held in the wall surface of the pin groove P20 to have the shape of a groove and protrusion, or a dovetail shape such that the stopper slides along the wall surface of the pin groove P20. Normally, as illustrated in FIG. 4, while the stopper P61 is raised by the elastic force of the stopping spring P63, a portion of the stopper P61 blocks a lower portion of the entrance of the seat groove P23, so the withdrawal of the insertion prevention member P40 from the seat groove P23 is prevented.

When the fastening pin P10 is fitted in the pin groove P20, the stopper P61 opens the entrance of the seat groove P23 by being pressed down and allows the withdrawal of the insertion prevention member from the seat groove P23.

Of course, to this end, a recess P131 defining space in which the stopping member P60 is located is formed in the body part P13 of the fastening pin P10, wherein a push step P133 for pressing the stopper P61 is preferably provided on the upper part of the recess P131.

In addition, to correspond to the thickness of the protection cover 25 to be fixed, the tank sterilizer of the present disclosure further includes a press member P70 composed of a press spring P73 provided on the lower surface of the head part P11 and a press plate P71.

For example, when the thickness of the protection cover 25 is thick, the compression rate of the press spring P73 increases, and when the thickness of the protection cover 25 is thin, the compression rate of the press spring P73 decreases, so that the fastening pin P10 is fitted in the pin groove P20 by maintaining a pressing force according to the thickness of the protection cover 25. More precisely, rather than the head part P11, the press plate P71 presses a surface of the protection cover 25 such that the fastening pin P10 is fitted in the pin groove P20.

In describing the present disclosure above, the tank sterilizer having specific shape, structure, and configuration has been mainly described with reference to the accompanying drawings, but the present disclosure may be variously modified, changed, and substituted by those skilled in the art. Such modification, change, and substitution should be construed as falling within the scope of the present disclosure.

What is claimed is:

1. A tank sterilizer comprising:
   a power supply part including a controller, a register, a changeover switch and a detection part;
   a sterilization part including a power connection module being electrically connected to the power supply part through a power supply line; and
   a bubble generation module mounted electrically and removably to the power connection module,
   wherein the power connection module comprises: a base, a protection cover coupled to the base by a fastening unit, a protrusion protruding inwardly from a center of the base, a bolting hole formed in the protrusion, a conductive insert nut provided inside the bolting hole, and a conductive bolt fastened to the conductive insert nut,
   wherein the power supply line is connected to the conductive bolt to supply a power to the bubble generation module, and the bubble generation module is seated on the protrusion and electrically connected to the conductive bolt such that the bubble generation module generates microbubbles and sterilizes fluid in a tank,
   wherein the fastening unit comprises:
   a fastening pin including: a body part passing through a coupling hole of the protection cover; and a head part provided on an upper part of the body part and pressing a surface of the protection cover, wherein the fastening pin includes a center groove formed in a center of the fastening pin and a withdrawal hole formed in a lower part of the center groove toward opposite sides thereof;

a pin groove formed in an inner flange part of the base to which the protection cover is coupled such that the fastening pin is fitted thereto, wherein a seat groove and a holding groove are formed at opposite surfaces of the pin groove such that each of the seat groove and the holding groove corresponds to the withdrawal hole; and a fastening member provided in the fastening pin, the fastening member fitting the fastening pin to the pin groove, wherein the fastening member includes: a fastening body part provided to be inserted into the center groove of the fastening pin and to be withdrawn through the withdrawal hole, the fastening body part having a magnet, a handlebar provided on the fastening body part and exposed to an upper side of the fastening pin through the center groove, and an insertion prevention member including a support block, a metal raising/lowering block coupled to the support block to raise and lower therefrom, and a raising induction spring giving an elastic force to the raising/lowering block, whereby, when the fastening member is advanced after being inserted to the center groove of the fastening pin, the fastening body is withdrawn through the withdrawal hole and inserted to the holding groove, so that the removal of the fastening pin is prevented, and when the fastening body is inserted to the holding groove, the insertion prevention member is pulled to the fastening pin by the magnet of the fastening body, and the raising/lowering block is raised from the support block by the raising induction spring and supports the inner wall surface of the center groove, so that a backward movement of the fastening member is limited, wherein the power connection module is provided in the tank such that a portion of each of the power connection module and the power supply line is immersed in the fluid, wherein the detection part transfers a detection current to the bubble generation module, and then detects a current value which varies according to an electrical conductivity of the fluid, and transfers the detected current value to the controller, wherein the controller compares the detected current value with threshold values stored therein to distinguish salt water from fresh water to thereby recognize whether the fluid is salt water or fresh water, and wherein, when the fluid is recognized as salt water, the changeover switch operates to transfer the detected current value to the register such that the detected current value is lowered to a set threshold value and then the lowered current is transferred to the bubble generation module, and when the fluid is recognized as fresh water, the changeover switch operates to allow the current to be transferred directly to the bubble generation module such that microbubbles are generated.

2. The sterilizer of claim 1, wherein the protection cover is provided with a plurality of discharge holes such that microbubbles generated by the bubble generation module are discharged, and the bubble generation module is provided with an electrode plate and a connection hole such that the connection hole is fastened to the bolting hole of the protrusion by the conductive bolt, thereby transferring electricity.

3. The sterilizer of claim 1, further comprising a cooling fan for preventing the register from overheating.

4. The sterilizer of claim 2, further comprising a cooling fan for preventing the register from overheating.

\* \* \* \* \*